US009759696B2

(12) United States Patent
Sezaki et al.

(10) Patent No.: US 9,759,696 B2
(45) Date of Patent: *Sep. 12, 2017

(54) CHANNEL BUBBLE REDUCTION DEVICE, CHANNEL BUBBLE REDUCTION METHOD, AND CHROMATOGRAPHY DEVICE

(71) Applicant: ARKRAY, Inc., Kyoto-shi (JP)

(72) Inventors: Akira Sezaki, Kyoto (JP); Tokuo Kasai, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 683 days.

This patent is subject to a terminal disclaimer.

(21) Appl. No.: 13/904,346

(22) Filed: May 29, 2013

(65) Prior Publication Data

US 2013/0319080 A1    Dec. 5, 2013

(30) Foreign Application Priority Data

May 30, 2012   (JP) ................................ 2012-123449

(51) Int. Cl.
| | |
|---|---|
| *G01N 30/02* | (2006.01) |
| *G01N 30/50* | (2006.01) |
| *B01D 15/16* | (2006.01) |
| *B01D 19/00* | (2006.01) |
| *G01N 30/26* | (2006.01) |
| *B01L 3/02* | (2006.01) |
| *G01N 30/20* | (2006.01) |
| *G01N 30/24* | (2006.01) |

(52) U.S. Cl.
CPC ............. *G01N 30/50* (2013.01); *B01D 15/16* (2013.01); *B01D 19/00* (2013.01); *B01D 19/0005* (2013.01); *B01L 3/0293* (2013.01); *G01N 30/26* (2013.01); *B01L 2200/0684* (2013.01); *B01L 2400/0622* (2013.01); *G01N 30/20* (2013.01); *G01N 30/24* (2013.01)

(58) Field of Classification Search
CPC ......... G01N 30/02; G01N 30/26; G01N 30/40
USPC ................. 422/70; 436/161; 210/198.2, 656; 73/61.56
See application file for complete search history.

(56) References Cited

U.S. PATENT DOCUMENTS

| | | | |
|---|---|---|---|
| 5,607,581 A | 3/1997 | Gerner et al. | |
| 9,285,347 B2 * | 3/2016 | Satake ............... | B01D 19/0063 |
| 2009/0149743 A1 * | 6/2009 | Barron .................. | A61M 5/007 |
| | | | 600/431 |

FOREIGN PATENT DOCUMENTS

| | | |
|---|---|---|
| EP | 0489569 A2 | 6/1992 |
| JP | S60-243562 A | 12/1985 |
| JP | H08-178806 A | 7/1996 |

(Continued)

OTHER PUBLICATIONS

Office Action dated Oct. 4, 2016 issued in the corresponding Japanese patent application No. 2013-113817.

*Primary Examiner* — Jan Ludlow
(74) *Attorney, Agent, or Firm* — Fox Rothschild LLP

(57) ABSTRACT

A channel bubble reduction device includes a liquid accommodation portion, that accommodates a liquid, a liquid supply apparatus that, with a pushing operation of a rod, discharges the liquid through an aperture portion of a tube portion, a first channel that connects the aperture portion of the liquid supply apparatus with the liquid accommodation portion, and an air layer formation apparatus that forms an air layer in at least one of the first channel or the tube portion.

6 Claims, 14 Drawing Sheets

(56) References Cited

FOREIGN PATENT DOCUMENTS

| | | |
|---|---|---|
| JP | 2007-212277 A | 8/2007 |
| JP | 2012-215450 A | 11/2012 |

* cited by examiner ent to a chromatography device may be provided, such that bubbles in a channel of the chromatography device may be effectively reduced.

CHANNEL BUBBLE REDUCTION DEVICE, CHANNEL BUBBLE REDUCTION METHOD, AND CHROMATOGRAPHY DEVICE

CROSS-REFERENCE TO RELATED APPLICATION

This application is based upon and claims the benefit of priority of the prior Japanese Patent Application No. 2012-123449, filed on May 30, 2012, the entire contents of which are incorporated herein by reference.

TECHNICAL FIELD

The present invention relates to a channel bubble reduction device, a channel bubble reduction method and a chromatography device.

BACKGROUND ART

Analysis devices that analyze components in samples include a chromatography device in which an analysis component in a sample is adsorbed to an adsorption portion such as a column or the like, an eluent is supplied to the adsorption portion and elutes the analysis component, and thereafter the component in the eluent is analyzed by a measurement device/process. This kind of chromatography device may include a degassing device that degasses the eluent by causing the eluent to flow in a spiral pipe in a low-pressure atmosphere, such that dissolved oxygen in the eluent passes through microscopic holes formed in the spiral tube (for example, Japanese Patent Application Laid-Open (JP-A) No. 2007-212277).

RELATED ART REFERENCES

Patent References

Patent Document 1: Japanese Patent Application Laid-Open (JP-A) No. 2007-212277

SUMMARY OF INVENTION

In consideration of the situation described above, an object of the present invention is to reduce bubbles in a channel.

A channel bubble reduction device according to a first aspect of the present invention includes: a liquid accommodation portion that accommodates a liquid; a liquid supply apparatus that, with a pushing operation of a rod, discharges the liquid through an aperture portion of a tube portion; a first channel that connects the aperture portion of the liquid supply apparatus with the liquid accommodation portion; and an air layer formation apparatus that forms an air layer in at least one of the first channel and the tube portion.

In this device for reducing bubbles in a channel, an air layer is formed by the air layer formation apparatus in the first channel and/or the tube portion. The air layer is caused to travel in the first channel by an operation of pushing of the rod. Hence, by the air layer traveling in the first channel, a portion (and preferably all) of bubbles adhering to an inner wall of the channel are taken into the air layer. Thus, bubbles in the first channel may be effectively reduced.

In a channel bubble reduction device according to a second aspect of the present invention, in the channel bubble reduction device according to the first aspect, the liquid supply apparatus discharges the air layer outside through the first channel with the pushing operation of the rod.

Accordingly, when the air layer is discharged outside the first channel, a state in which none of the air layer remains in the first channel may be achieved, and there is no effect from the air layer when a liquid from inside the first channel is used. Moreover, the air layer may be discharged outside the first channel by a simple operation, of simply pushing the rod.

In a channel bubble reduction device according to a third aspect of the present invention, in the channel bubble reduction device according to the first or second aspect, the air layer formation apparatus includes: an atmosphere release aperture provided at one of the first channel and the tube portion; and an opening and closing valve capable of opening and closing the atmosphere release aperture, and the liquid supply apparatus introduces air through the atmosphere release aperture into the at least one of the first channel and the tube portion with a pulling operation of the rod.

That is, by pulling of the rod in the state in which the opening and closing valve is open and the atmosphere release aperture is opened, air may be introduced through the atmosphere release aperture to the first channel and/or the tube portion, and the air layer may be formed. Thus, because the air layer formation apparatus may in essence be structured by the atmosphere release aperture and the opening and closing valve, the structure may be made simple.

In a channel bubble reduction device according to a fourth aspect of the present invention, in the channel bubble reduction device according to the first or second aspect, the air layer formation apparatus includes a movement apparatus that relatively moves a liquid intake aperture at the liquid accommodation portion side of the first channel between a submerged position at which the liquid intake aperture is submerged in the liquid and a separated position at which the liquid intake aperture is separated from the liquid, and the liquid supply apparatus introduces air through the liquid intake aperture at the separated position into the at least one of the first channel and the tube portion with a pulling operation of the rod.

That is, by pulling of the rod in the state in which the liquid intake aperture of the first channel has been set to the separated position by the movement apparatus, air may be introduced through the liquid intake aperture to the first channel, and the air layer may be formed. After the air layer is formed, the liquid intake aperture may be set to the submerged position and the liquid may be taken into the first channel. Thus, because the air layer formation apparatus may in essence be structured by the movement apparatus, the structure may be made simple.

A channel bubble reduction program according to a fifth aspect of the present invention causes a computer to execute a process including: an air layer formation procedure in which an air layer is formed by an air layer formation apparatus in at least one of a first channel and a tube portion, the first channel connecting a liquid accommodation portion with a liquid supply apparatus, the liquid accommodation portion accommodating a liquid, and the liquid supply apparatus discharging the liquid through an aperture portion of the tube portion with a pushing operation of a rod; and an air layer travel procedure in which the air layer formed in the air layer formation procedure is caused to travel in the first channel by the pushing operation of the rod.

According to this program for reducing bubbles in a channel, in the air layer formation procedure, an air layer is formed in the first channel by the air layer formation apparatus. Then, in the air layer travel procedure, the air layer is caused to travel in the first channel by an operation of pushing of the rod. Thus, by the air layer traveling in the first channel, a portion of (preferably all) the bubbles in the channel are taken into the air layer. Thus, bubbles in the first channel may be effectively reduced. That is, bubbles in the first channel may be decreased by the operations of forming the air layer in the first channel and/or the tube portion and causing the air layer to travel.

A channel bubble reduction method according to a sixth aspect of the present invention includes: an air layer formation step of forming an air layer in at least one of a first channel and a tube portion, the first channel connecting a liquid accommodation portion with a liquid supply apparatus, the liquid accommodation portion accommodating a liquid, and the liquid supply apparatus discharging the liquid through an aperture portion of the tube portion with a pushing operation of a rod; and an air layer travel step of causing the air layer formed in the air layer formation step to travel in the first channel by the pushing operation of the rod.

In this method for reducing bubbles in a channel, in the air layer formation step, an air layer is formed in the first channel. In the air layer travel step, the air layer is caused to travel in the first channel by an operation of pushing of the rod. Thus, by the air layer traveling in the first channel, a portion of (preferably all) the bubbles in the channel are taken into the air layer. Thus, bubbles in the first channel may be effectively reduced. That is, bubbles in the first channel may be decreased by the operations of forming the air layer in the first channel and/or the tube portion and causing the air layer to travel.

In a channel bubble reduction method according to a seventh aspect of the present invention, in the channel bubble reduction method according to the sixth aspect, the air layer travel step includes discharging the air layer outside through the first channel.

That is, when the air layer is discharged outside through the first channel, a state in which none of the air layer remains in the first channel may be achieved, and there is no effect from the air layer when a liquid from inside the first channel is used. Moreover, the air layer may be discharged outside the first channel by a simple operation, of simply pushing the rod.

A liquid provision device according to an eighth aspect of the present invention includes: a channel bubble reduction device according to one of the first to fifth aspects; a second channel branching from the first channel; and a first switching valve provided at the second channel branching portion and capable of switching to put the liquid supply apparatus side of the first channel into fluid communication with either of the liquid accommodation portion side and the second channel side.

In the state in which the first switching valve is switched to the liquid accommodation portion side, the air layer is caused to travel in the first channel by the pushing operation of the rod, and bubbles in the first channel may be reduced.

In the state in which the first switching valve is switched to the second channel side, the liquid may be supplied through the second channel to the adsorption portion by the pushing operation of the rod. That is, simply by switching of the first switching valve, both the reduction of bubbles in the first channel and the supply of liquid to the adsorption portion may be implemented by the pushing operation of the rod.

A chromatography device according to a ninth aspect of the present invention includes: the liquid provision device according to the eighth aspect; an adsorption portion that adsorbs an analysis component in the liquid supplied by the liquid provision device; and an analysis device that analyzes the analysis component, which is eluted by the liquid supplied to the adsorption portion by the liquid provision device.

Using the liquid provision device, the liquid is supplied to the adsorption portion, and an analysis component is adsorbed. Then, the analysis component may be eluted from the adsorption portion by a liquid supplied to the adsorption portion by the liquid provision device, and the analysts component may be analysed by the analysis device. Because the liquid provision device includes the channel bubble reduction device and reduces bubbles in a channel, the effects of bubbles on analysis at the analysis device may be reduced. Furthermore, because the channel bubble reduction device may be reduced in size, the chromatography device itself may be reduced in size.

DESCRIPTION OF EMBODIMENTS

First Exemplary Embodiment

Overall Structure

Herebelow, exemplary embodiments of the present invention are described with reference to the attached drawings.

Figure 1:
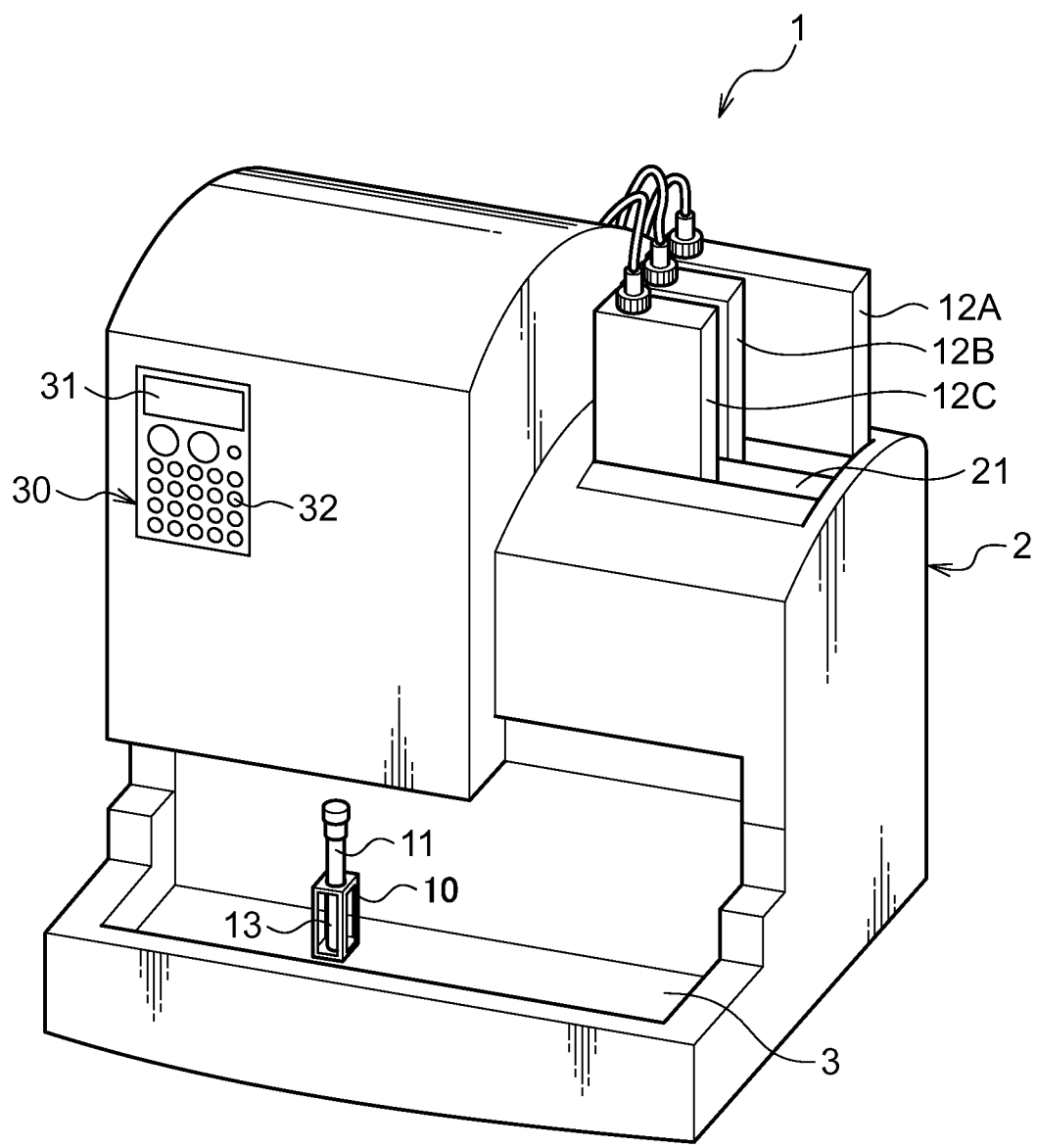
FIG. 1 is a perspective view showing the exterior of a chromatography device equipped with a liquid provision device that includes a channel bubble reduction device in accordance with a first exemplary embodiment of the present invention.
Figure 2:
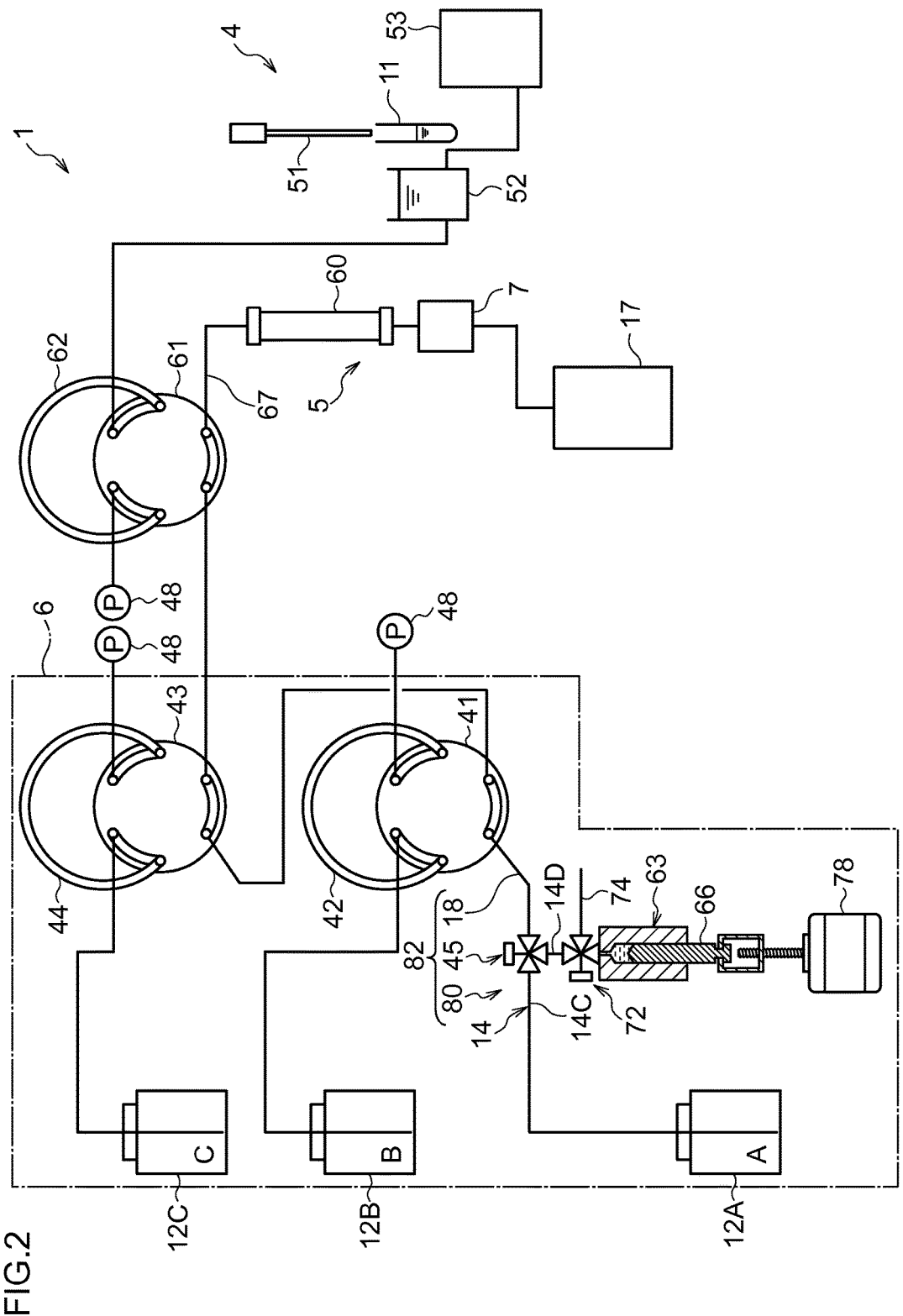
FIG. 2 is a schematic diagram showing internal structures of the chromatography device equipped with the liquid provision device that includes the channel bubble reduction device in accordance with the first exemplary embodiment of the present invention.
Figure 3:
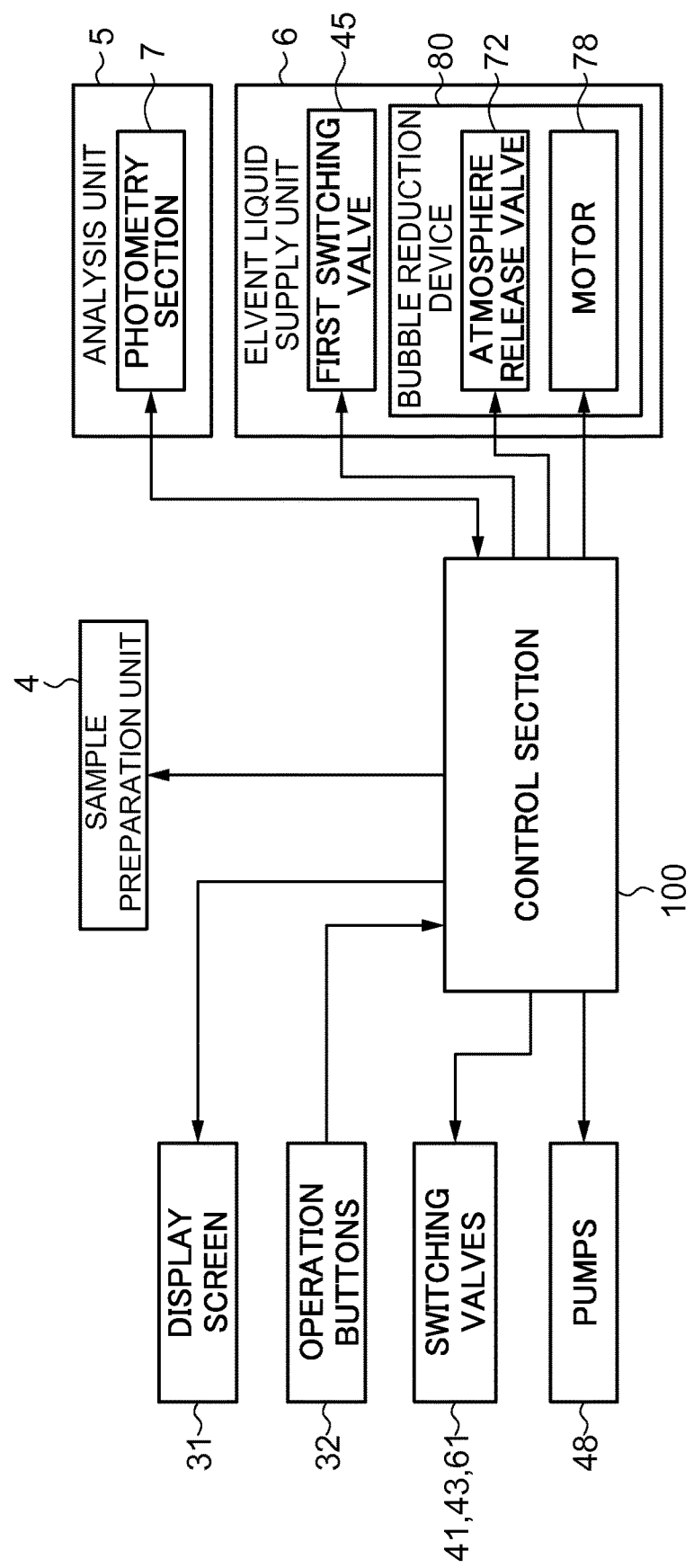
FIG. 3 is a block diagram showing structures of the chromatography device equipped with the liquid provision device that includes the channel bubble reduction device in accordance with the first exemplary embodiment of the present invention.

FIG. 1 and FIG. 2 show a chromatography device 1 including a liquid provision device 82 that is provided with a channel bubble reduction device 80 according to a first exemplary embodiment of the present invention. FIG. 3 shows a block diagram of structures of the chromatography device 1. The chromatography device 1 is a device that carries out fully automatic high-performance liquid chromatography (HPLC), which uses an eluent to measure glycohemoglobin concentrations in whole blood.

As shown in FIG. 1, the chromatography device 1 is equipped with a device main body 2 that serves as a casing. The liquid provision device 82 (see FIG. 2 and FIG. 4), a sample preparation unit 4 (see FIG. 2), an analysis unit 5 (see FIG. 2) and the like, which are described below, are accommodated in the device main body 2.

A table 3 is provided at a lower portion of the device main body 2. A rack 10 holding a blood collection tube 11 is placed on the table 3. A sample, which is blood, is accommodated in the blood collection tube 11. This sample is a specimen that is to be subject to glycohemoglobin concentration detection in the chromatography device 1 according to the present exemplary embodiment. The present exemplary embodiment has a structure that carries out analysis of a single blood collection tube 11 with a single measurement, but this is not limiting. A rack that can hold a plural number of the blood collection tube 11 may be used and measurements may be carried out successively.

A holder portion 21, which is formed of a plural number of recessed portions, is formed at an upper portion at one width direction end side of the device main body 2 (the right side in FIG. 1). In the holder portion 21 are placed eluent packs 12, which serve as a liquid accommodation portion, accommodating eluents of respectively different types (referred to herein for the sake of convenience as three types, eluents A, B and C). Specifically, in the holder portion 21 are placed, respectively, an eluent pack 12A accommodating the eluent A, an eluent pack 12B accommodating the eluent B, and an eluent pack 12C accommodating the eluent C. The eluents accommodated in the eluent packs 12A, 12B and 12C have respectively different pH values and salt concentrations and the like, and are for eluting respective analysis components that have adsorbed to a packing material of a column 60, which is described below. Beside the eluent packs 12, other containers may be placed in the holder portion 21, such as a washing fluid bottle that accommodates a washing fluid for washing piping and the like.

An operation panel 30 is provided at an upper portion of the other width direction end side (the left side in FIG. 1) of the device main body 2. The operation panel 30 includes plural operation buttons 32 and a display screen 31. As shown in FIG. 3, the operation buttons 32 and the display screen 31 are connected to a control section 100, which serves as a computer. In accordance with operations of the operation buttons 32, operation information is sent to the control section 100 and analysis conditions and the like may be specified. The display screen 31 receives information from the control section 100, and analysis results, errors, operation states and the like are displayed at the display screen 31.

As shown in FIG. 2, the chromatography device 1 is principally structured with the sample preparation unit 4, the analysis unit 5 and an eluent liquid supply unit 6. The sample preparation unit 4 is a unit that prepares a blood specimen to be supplied to the analysis unit 5. The sample preparation unit 4 is equipped with a nozzle 51 that sucks up a blood specimen 13, a preparation fluid tank 53, and a diluent tank 52 that prepares the blood specimen 13. At an appropriate timing, the blood specimen 13 is supplied from the sample preparation unit 4 to the column 60 via a switching valve 61.

The analysis unit 5 is a unit that measures a concentration of glycohemoglobin in the blood specimen. The analysis unit 5 is equipped with the column 60 and a photometry section 7. The column 60 is a tube into which a packing material (not shown in the drawings) that adsorbs a specific component (glycohemoglobin) in the blood specimen is packed. The column 60 is formed of glass, stainless steel or resin. In the present exemplary embodiment, as an example, the column 60 that is used is made of stainless steel. The photometry section 7 is a section that shines light onto the eluent passed through the column 60, and optically detects hemoglobin from the wavelengths of light that is transmitted through the eluent. The photometry section 7 is structured with a light source and a light detection unit or the like. Data from the photometry section 7 is sent to the control section 100 and displayed at the display screen 31.

The eluent liquid supply unit 6 is a unit that sucks eluent from the eluent packs 12A, 12B and 12C and supplies the eluents to the column 60 of the analysis unit 5. The eluent liquid supply unit 6 includes a plunger pump 63 of the channel bubble reduction device 80 that structures the liquid provision device 82, two switching valves 41 and 43, and piping.

The switching valves 41, 43 and 61 are all valves at which flowpaths may be switched, and are controlled by the control section 100, as shown in FIG. 3. Pumps 48 are connected to the respective switching valves 41, 43 and 61. If the pumps 48 are driven in the state shown in FIG. 2, the switching valves 41, 43 and 61 supply the eluent B, the eluent C and the blood specimen 13 to loop pipes 42, 44 and 62, respectively.

The plunger pump 63 sucks the eluent from the eluent pack 12A and supplies the eluent at a constant rate. Piping structures in which the loop pipes 44 and 62 are in fluid communication with a pipe 67 can be formed by the control section 100 switching the switching valves 43 and 61 at predetermined timings. Thus, the eluents B and C can be pushed by the eluent A supplied from the plunger pump 63 and can be supplied to the column 60.

In the chromatography device 1, the sample preparation unit 4, the analysis unit 5, the eluent liquid supply unit 6 and the liquid provision device 82 may be accommodated in a single casing (the device main body 2), but the overall structure of the chromatography device 1 is not limited thus. For example, the sample preparation unit 4, the analysis unit 5, the eluent liquid supply unit 6 and the liquid provision device 82 may be structured as respectively separate units and made to function as a system by being connected.

—Structure of Bubble Reduction Device—

Now, the structure of the channel bubble reduction device 80 according to the present exemplary embodiment is described. As is shown in detail in FIG. 4, the channel bubble reduction device 80 includes the plunger pump 63, the eluent pack 12A, a first channel 14 that connects the plunger pump 63 with the eluent pack 12A, and an atmosphere release valve 72 that serves as an air layer formation apparatus provided at the first channel 14.

The first channel 14 connecting the eluent pack 12A with the plunger pump 63 is structured by two pipes 14D and 14C being serially connected. The pipes 14C and 14D are connected by a first switching valve 45, which is controlled by the control section 100.

The plunger pump 63 is provided with a syringe 65, which serves as a tube portion, in fluid communication with the pipe 14D at the plunger pump 63 side of the pipe 14D. The syringe 65 is a member made of stainless steel, of which upper and lower end portions are open. An inner wall 65C with a constant diameter is formed from an aperture 65A at the lower end side of the syringe 65 to an upper portion of the syringe 65. An upper portion of the inner wall 65C of the syringe 65 forms a taper surface that tapers upward toward an aperture portion 65B at the upper end portion of the syringe 65. The aperture portion 65B is connected to the pipe 14D. The syringe 65 may be formed of a metal other than stainless steel, and may be formed of a resin.

The aperture portion 65B opens in an upward orientation. In the example shown in the drawings, the orientation is perpendicularly upward, but the orientation does not strictly need to be perpendicularly upward. It is sufficient that the orientation be upward such that air in the syringe 65 can be discharged at an early stage during an operation of pushing a plunger 66, as described below. For example, a structure in which the syringe 65 is disposed at an angle and the aperture portion 65B is formed to be oriented diagonally upward is to be encompassed. Further, provided the structure forms an air layer AR in the first channel 14 and the air layer AR can be caused to travel in the first channel 14, the aperture portion 65B may be opened to, for example, a downward (or diagonally downward) orientation or a lateral orientation or the like.

The plunger 66 is disposed at the inside of the syringe 65. The plunger 66 serves as a rod that is movable in the up-and-down direction. An outer diameter of the plunger 66 is substantially the same as an inner diameter of the syringe 65, and the plunger 66 slides along the inner periphery face of the syringe 65. An upper end portion of the plunger 66 is formed in a conical shape similar to that of the upper portion of the inner wall 65C of the syringe 65. The plunger 66 is designed so as to make area contact with the syringe 65 when the plunger 66 is pushed up to the upper end side, without a gap between the syringe 65 and the plunger 66. An O-ring is attached to the plunger 66, such that fluids inside the syringe 65 do not leak from the aperture 65A.

An annular groove 66A is formed at a lower end portion of the plunger 66. An attachment hole 68A is formed in an upper face of a plunger retention member 68. A hole edge of the attachment hole 68A engages with the annular groove 66A. A ball screw 70 is threaded into a lower face of the plunger retention member 68. The ball screw 70 is connected to a rotary shaft of a motor 78.

When the control section drives the motor 78, the ball screw 70 rotates, the plunger retention member 68 moves in the up-and-down direction and moves the plunger 66, and space inside the syringe 65 is increased or reduced. In the present exemplary embodiment, a stepper motor is used as an example of the motor 78, but this is not limiting; a servo motor or the like may be used.

The first switching valve 45 connecting the pipe 14D and pipe 14C of the first channel 14 is a solenoid valve (a three-way valve) that may open and close arbitrary pipes in accordance with driving of a solenoid. The lengths of the pipe 14D and the pipe 14C are specified such that, as in the example shown in the drawings, the location of the first switching valve 45 is a location on the first channel 14 that is close to the plunger pump 63.

The first switching valve 45 and the column 60 are connected by a second channel 18. In essence, the first switching valve 45 is provided at a branching portion between the first channel 14 and the second channel 18.

A channel structured by the piping, that is, a state of communication between the first channel 14 and the second channel 18, can be switched by switching of the first switching valve 45. Specifically, it is possible to switch between a state in which the pipe 14D and pipe 14C of the first channel 14 are in fluid communication while the second channel 18 is closed off (a first communication state, see FIG. 4 to FIG. 7) and a state in which the pipe 14D of the first channel 14 and the second channel 18 are in fluid communication while the pipe 14C is closed off (a second communication state, see FIG. 9). Obviously, a structure is also possible that may, depending on circumstances, go into a state in which the pipe 14C and the second channel 18 are in fluid communication while the pipe 14D is closed off.

In the first exemplary embodiment, the atmosphere release valve 72, controlled by the control section, is provided on the pipe 14D of the first channel 14. An atmosphere release pipe 74 is connected to the atmosphere release valve 72. A distal end of the atmosphere release pipe 74 is open to the atmosphere. In the present exemplary embodiment, the atmosphere release valve 72 is a solenoid valve (a three-way valve) similar to the first switching valve 45. The atmosphere release valve 72 can be switched between a usual state in which the atmosphere release pipe 74 side thereof is closed while the pipe 14D is in fluid communication with the plunger pump 63 (a liquid supply-enabled state) and a state in which the pipe 14D side is closed off while the atmosphere release pipe 74 is in fluid communication with the plunger pump 63 (an air introduction-enabled state).

In particular, in the example shown in the drawings the atmosphere release valve 72 is specified to be at a location of the pipe 14D that is close to the plunger pump 63. It is not necessary for the atmosphere release valve 72 to be a three-way valve, provided the atmosphere release valve 72 may open and close an atmosphere release aperture (in the example shown in the drawings, the atmosphere release pipe 74). The atmosphere release valve 72 may be a simple opening and closing valve.

As shown in FIG. 3, the motor 78, the atmosphere release valve 72, the first switching valve 45 and the pumps 48 are electronically connected to the control section 100 and are driven by instructions from the control section 100.

The control section 100 is equipped with a CPU, ROM, RAM, memory, an input/output port, a network interface, and a bus connecting all these (none of which are shown in the drawings). The control section 100 is a computer of the present invention. The CPU administers overall control of the chromatography device 1. The ROM stores a program for supplying predetermined eluents and the blood specimen 13 by switching the switching valves 41, 43 and 61 as mentioned above, driving the pumps 48 and driving the plunger pump 63. The ROM also stores a program for driving the plunger pump 63 such that the air layer AR is formed in the first channel 14 and/or the syringe 65, as mentioned above, and the air layer AR is caused to travel in the first channel 14. The RAM serves as a work area and may temporarily store various kinds of data. Various kinds of information are stored in the memory. The display screen 31 and the operation buttons 32 are connected to the input/output port.

—Automatic Analysis Process—

Figure 14:
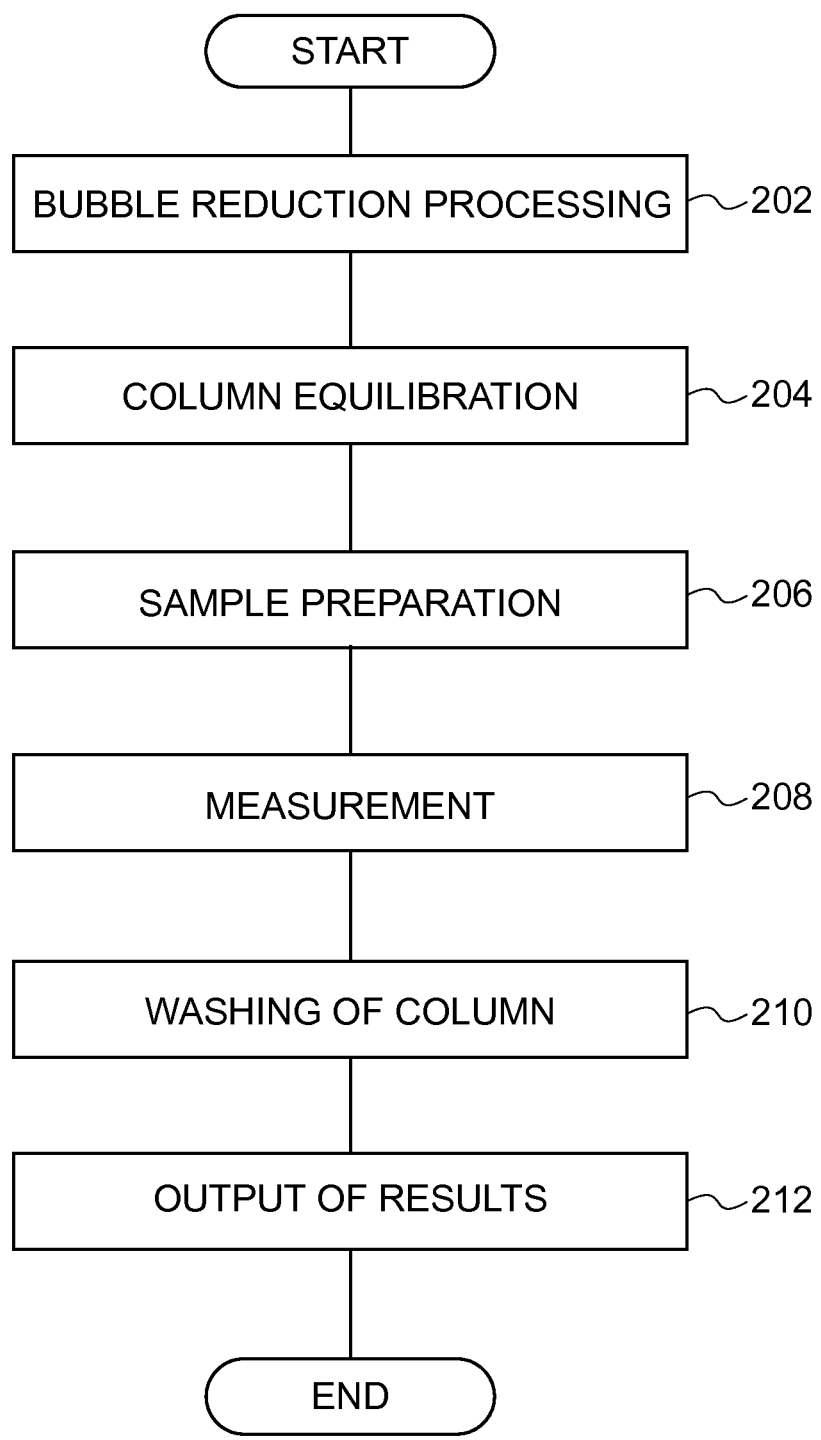
FIG. 14 is a flowchart showing an automatic analysis procedure of the liquid chromatography device in accordance with the first exemplary embodiment of the present invention.

Now, a process of automatic analysis by the chromatography device 1 is described based on the block diagram of FIG. 3 and the flowchart of FIG. 14. The following automatic analysis process is a chromatography process for analyzing analysis components contained in a sample of blood or the like. First, when a user operates the operation panel 30 or instructs the control section 100 to start the chromatography device 1 from a keyboard or the like, the control section 100 executes an automatic analysis program. Then, in step 202, the control section 100 controls the bobble reduction device 80 to perform bubble reduction processing. In the present exemplary embodiment, by performing bubble reduction processing prior to performing photometry at the photometry section 7 with respect to the eluent, dissolved oxygen in the eluent can be reduced and generation of noise at the photometry section 7 can be suppressed. The specifics of the bubble reduction processing are described below.

Next, in step 204, the control section 100 controls the eluent liquid supply unit 6 to perform equilibration of the column 60. Here, equilibration is performed by supplying the eluent A to the column 60 until the filler material of the column 60 is smoothly coated. Specifically, the eluent A, after if has been subjected to bubble reduction processing and drawn in by the plunger pump 63 of the eluent liquid supply unit 6, is ejected by the plunger 66 and supplied to the column 60. Further, the time taken to discharge the eluent A is set in advance in accordance with the type or the like of the column 60. When equilibration of the column 60 is complete, the process proceeds to step 206. In step 206, the control section 100 controls the sample preparation unit 4 to perform sample preparation. Specifically, the nozzle 51 of the sample preparation unit 4 suctions the blood specimen 13 from the blood collection tube 11 and drops the blood specimen 13 into the diluent tank 52. The blood specimen 13 is hemolyzed and diluted in the diluent tank 52 with the preparation fluid from the preparation fluid tank 53, and is extracted by the pump 48 and fed into the loop pipe 62 at the switching valve 61.

Next, in step 208, the control section 100 controls the analysis unit 5 to perform measurement. Here, in accordance with an instruction from the control section 100, the photometry section 7 of the analysis unit 5 starts analysis. Further, a certain time after the eluent A has been supplied to the column 60, switching valve 61 is operated to switch the flowpath of the eluent A, and the blood specimen 13 inside the loop pipe 62 is ejected with the eluent A and supplied to the column 60.

An analysis component in the specimen is adsorbed to the packing material of the column 60, and the residue of the specimen passes through the photometry section 7 and is drained to the waste liquid tank 17. Thereafter, the eluent A elutes a portion of the analysis component that has been adsorbed to the packing material of the column 60, and is supplied to the photometry section 7. The photometry section 7 detects the analysis component(s) in the eluent A and sends data thereof to the control section.

When the elution of an analysis component by the eluent A is completed, the switching valve 43 is switched and the flowpath of the eluent A is altered. Hence, the eluent C in the loop pipe 44 is pushed out by the eluent A and supplied to the column 60. The eluent C elutes an analysis component that has not been eluted by the eluent A, and passes through the photometry section 7.

When the elution of an analysis component by the eluent C is completed, the switching valve 41 is switched and the flowpath of the eluent A is altered. Hence, the eluent B in the loop pipe 42 is pushed out by the eluent A and supplied to the column 60. The eluent B elutes an analysis component that has not been eluted by the eluents A and C, and passes through the photometry section 7.

Thus, analysis components its a blood specimen are separated out and subjected to qualitative and quantitative analyses. In the present exemplary embodiment, the chromatography device 1 has a structure that performs automatic analysis when the chromatography device 1 is started, but this is not limiting; analyses may be conducted manually, in which case a user switches the switching valves 41, 43 and 61 at arbitrary timings.

When the measurement is complete, the process proceeds to step 210. In step 210, the control section 100 controls the eluent liquid supply unit 6 to perform cleaning of the column 60. Specifically, equilibration is performed by supplying the eluent A to the column 60 and washing out any analysis component attached to the filler material of the column 60.

Finally, in step 212, analysis data sent from the photometry section 7 to the control section 100 is compiled and output as analysis results. The analysis results are displayed at the display screen 31 and/or other monitors. Further, when sample analysis is performed in succession, analysis is performed in the same sequence from the bubble reduction processing of step 202.

—Bubble Reduction and Liquid Supply Procedure—

Figure 6:
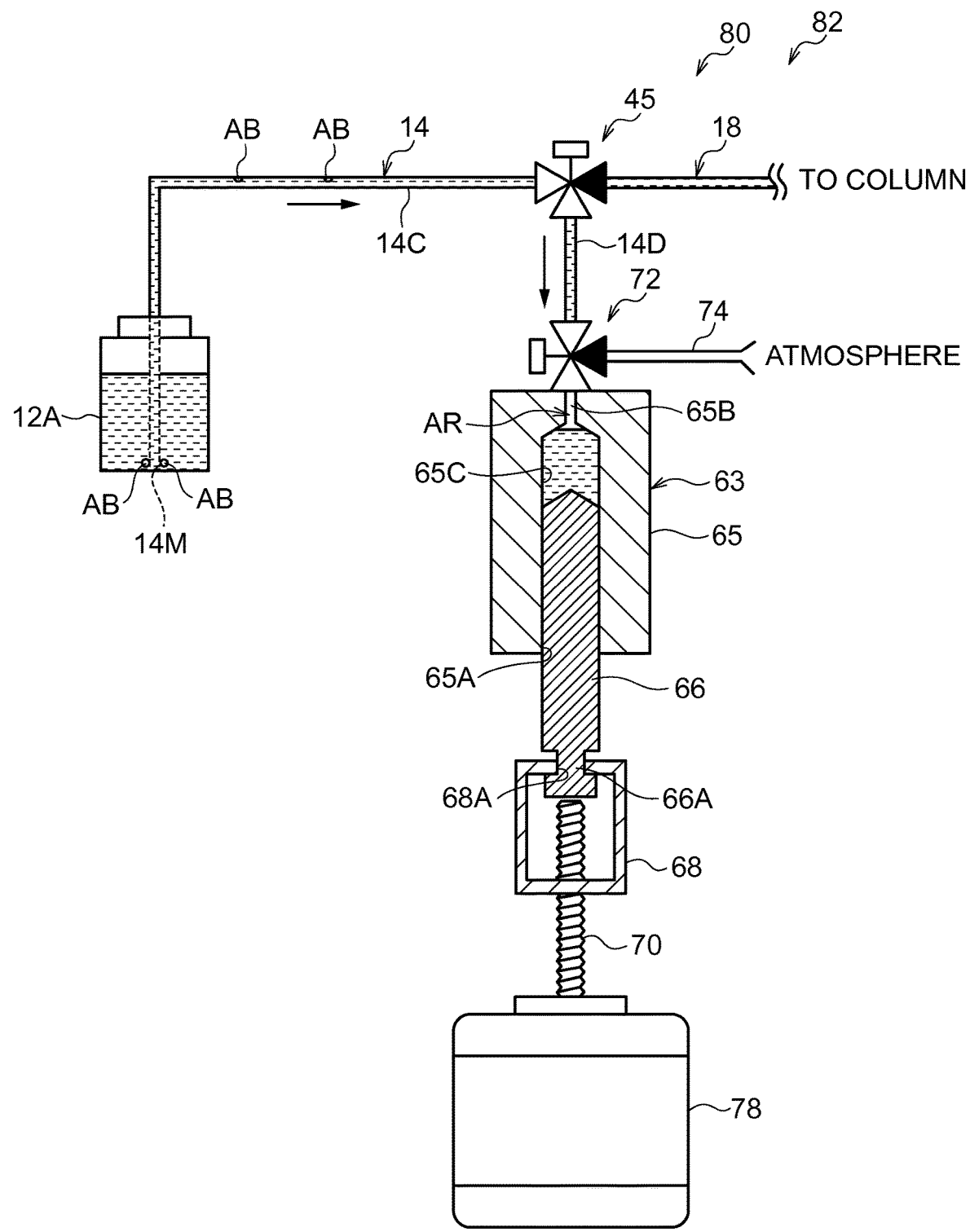
FIG. 6 is an enlarged diagram of principal portions, showing a state after the air layer has been formed by the channel bubble reduction device in accordance with the first exemplary embodiment of the present invention.
Figure 7:
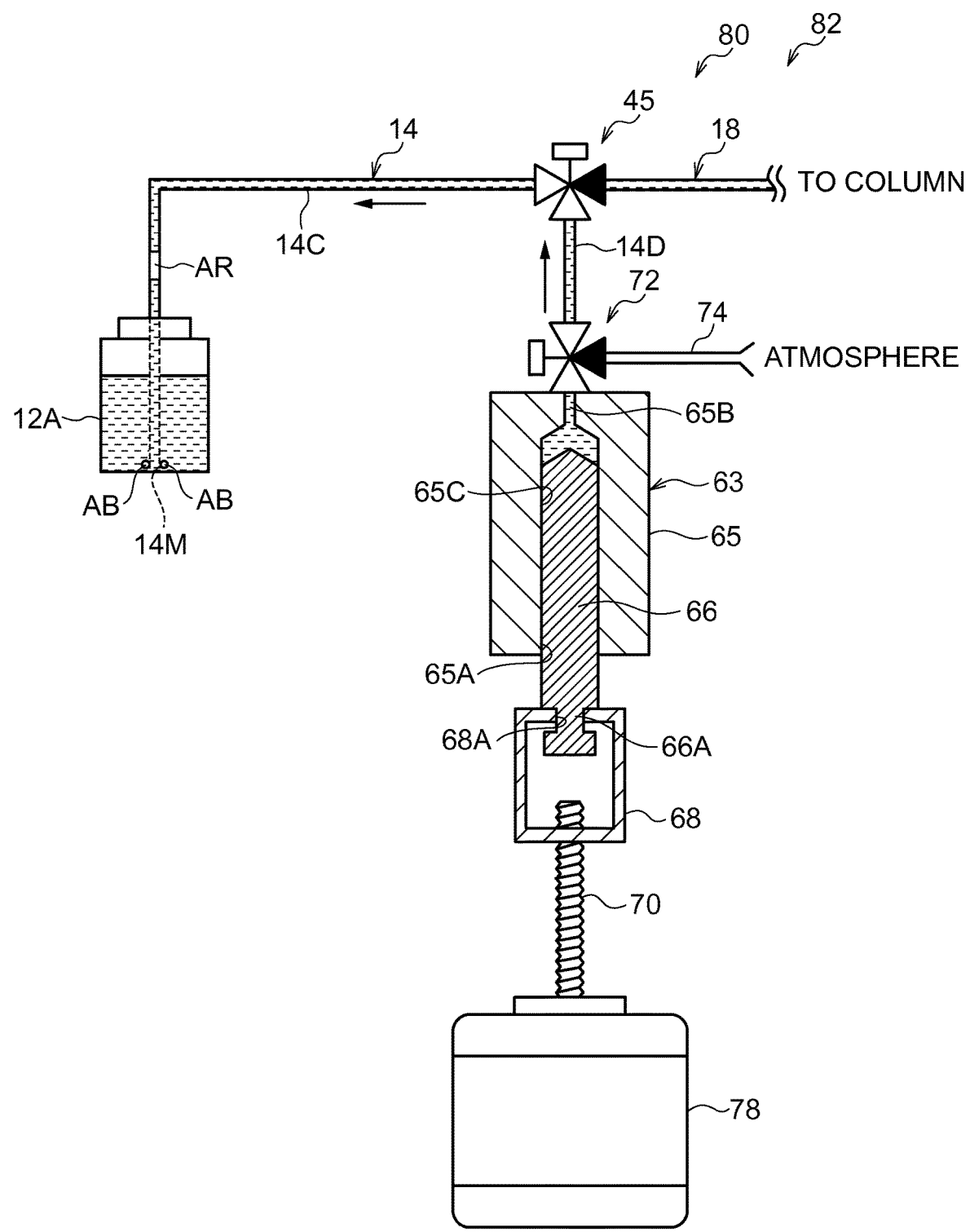
FIG. 7 is an enlarged diagram of principal portions, showing a state in which the air layer is being pushed out by the channel bubble reduction device in accordance with the first exemplary embodiment of the present invention.
Figure 8:
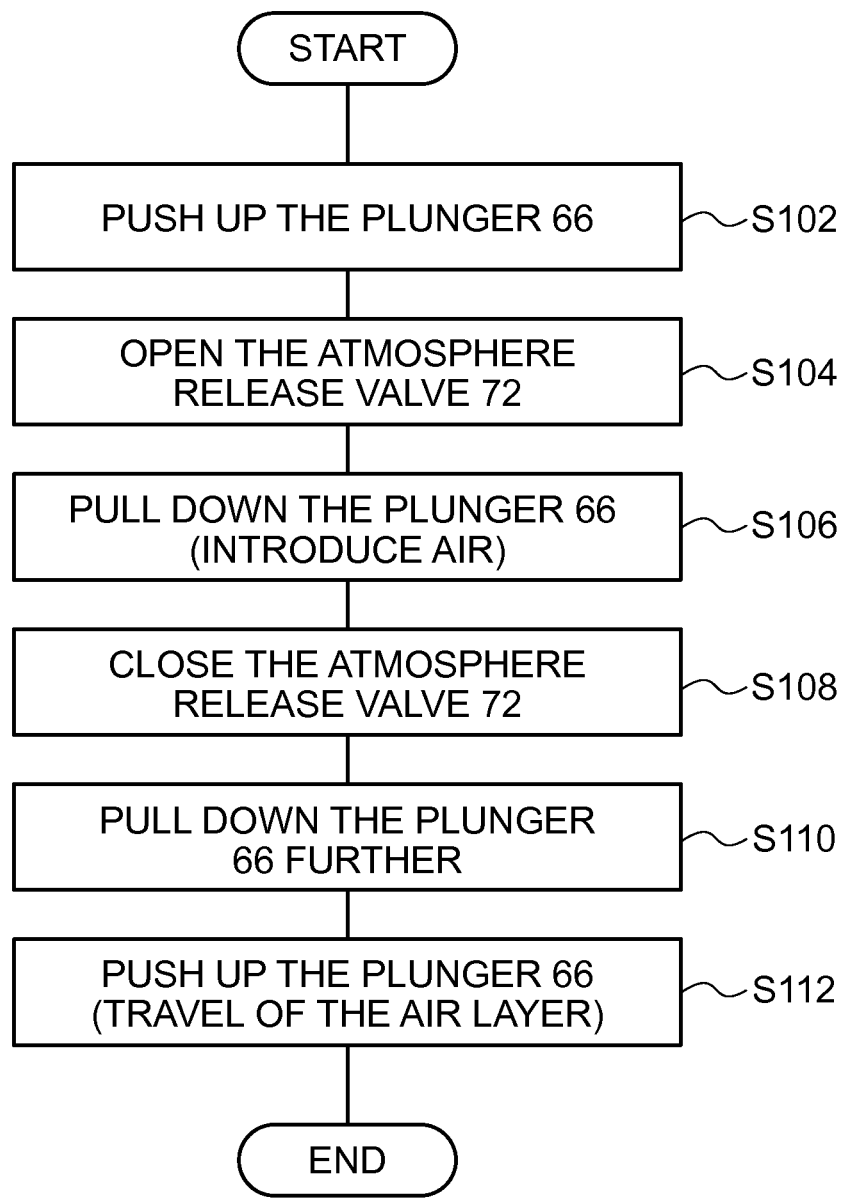
FIG. 8 is a flowchart showing a process for reducing bubbles in a channel with the channel bubble reduction device in accordance with the first exemplary embodiment of the present invention.

Now, a procedure for reducing bubbles in an eluent and supplying the eluent (liquid provision) with the channel bubble reduction device 80 is described in accordance with the flowchart in FIG. 8. In FIG. 4 to FIG. 7, where appropriate for description, open valves are shown white and closed valves are shown solid black.

Because oxygen is mixed into the eluent, the dissolved oxygen gasifies and forms bubbles AB. In particular, because pressure in the first channel 14 is lower than pressure in the second channel 18, dissolved oxygen more easily becomes bubbles AB in the first channel 14. It is desirable to suppress supplies of bubbles AB to the photometry section 7 with the eluent, to reduce the effects of the bubbles AB on measurement results.

Figure 4:
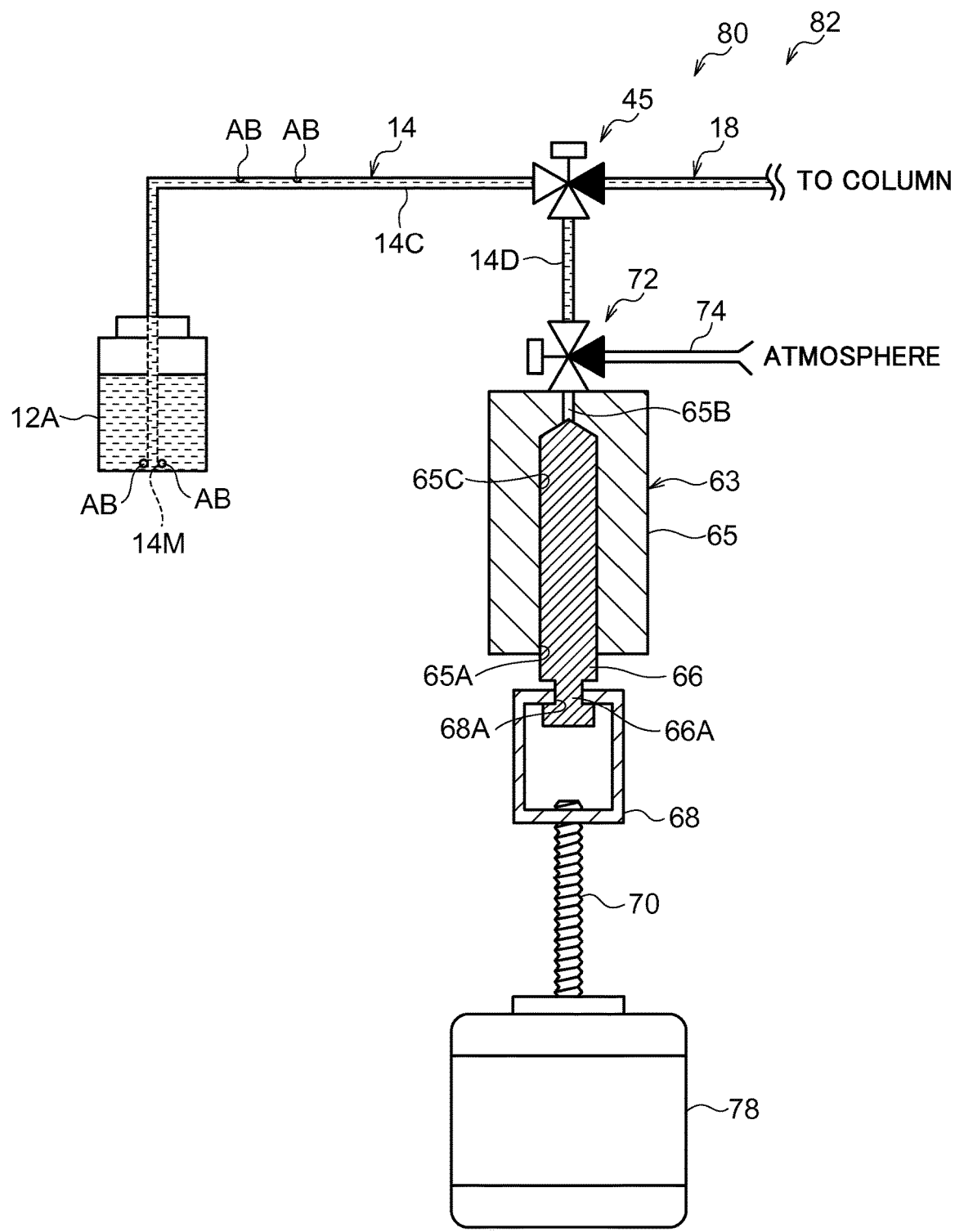
FIG. 4 is an enlarged diagram of principal portions, showing a state before an air layer is formed by the channel bubble reduction device in accordance with the first exemplary embodiment of the present invention.

In the present exemplary embodiment, to remove the bubbles AB from inside the first channel 14, the first switching valve 45 is put into the first communication state and the atmosphere release valve 72 is put into the closed state. In this state, as shown in FIG. 4, the plunger 66 of the plunger pump 63 is pushed up in step S102. However, there is no need to push up the plunger 66 if an amount by which the plunger 66 is pulled down allows an excess (margin) such that, as described below, air can be introduced into the syringe 65 and the eluent can be introduced. At this stage, the first switching valve 45 may be in the second communication state.

Figure 5:
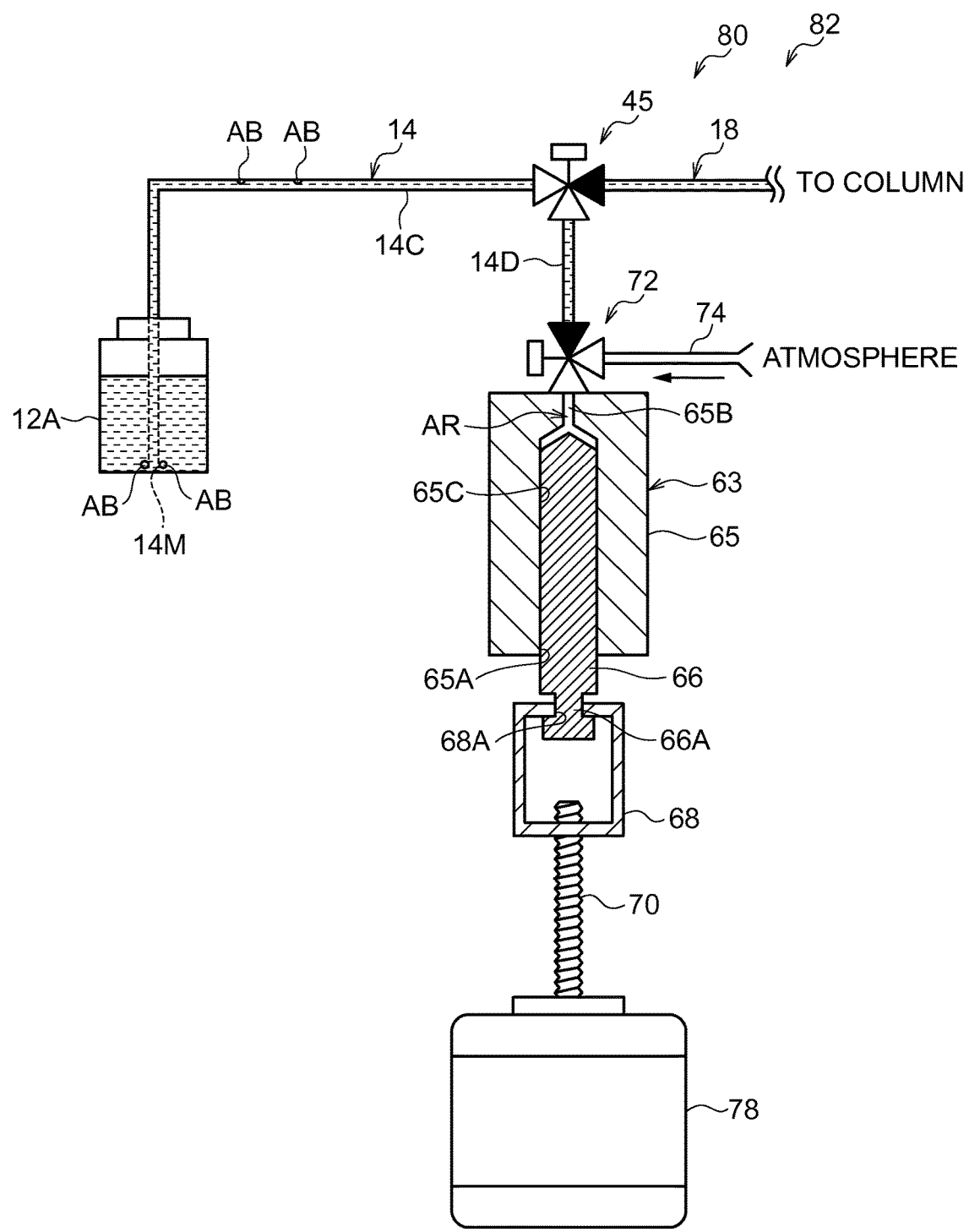
FIG. 5 is an enlarged diagram of principal portions, showing a state in which the air layer is being formed by the channel bubble reduction device in accordance with the first exemplary embodiment of the present invention.

Then, in step S104 the atmosphere release valve 72 is opened, and in step S106 the plunger 66 is pulled down. Accordingly, air is introduced into the pipe 14D of the first channel 14 through the atmosphere release pipe 74. Consequently, as shown in FIG. 5, the air layer AR is formed in the pipe 14D and in the syringe 65 (an air layer formation step). The amount of air in this air layer AR is an amount such that, when traveling in the first channel 14 as described below, air (gas) is continuous in the circumferential direction at the inner periphery of the first channel 14, and such that the air layer AR is not excessively long in the longitudinal direction of the first channel 14. In practice, the amount of air in the air layer AR is adjusted by the amount by which the plunger 66 is pulled down being set to a predetermined amount.

When this predetermined air layer AR has been formed, in step S108 the atmosphere release valve 72 is closed (and if the first switching valve 45 has been put into the second communication state, the first switching valve 45 is switched to the first communication state).

In step S110, the plunger 66 is pulled down further. Because the atmosphere release valve 72 is closed, air is not introduced but, as shown in FIG. 6, the eluent flows into the syringe 65. The amount of this eluent is an amount such that, as described below, the plunger 66 may be pushed up, cause the air layer AR to travel along the first channel 14, and discharge the air layer AR into the eluent pack 12A. For the eluent too, the amount of eluent in the syringe 65 may be adjusted by the amount by which the plunger 66 is pulled down being set to a predetermined amount.

The plunger 66 is pulled down as a single operation (a continuous pulling-down operation) in steps S106 to S110, and the atmosphere release valve 72 is closed during this operation. Thus, this procedure may be carried out smoothly.

When the predetermined amount of eluent is collected in the syringe 65, the air layer AR is in an upper layer in the syringe 65 and the eluent is in a lower layer.

Then, in step S112, the plunger 66 is pushed up. Because the plunger pump 63 is formed with the aperture portion 65B oriented upward, when the plunger 66 is pushed up, firstly, the air layer AR travels in the first channel 14. In particular, because the shape of the inner wall of the upper portion of the syringe 65 is formed as a taper toward the aperture portion 65B, the air layer AR is not broken up when being discharged but is evacuated smoothly without remaining in the syringe 65.

Then, as the plunger 66 continues to be pushed up, as shown in FIG. 7, the air layer AR travels in the first channel 14 toward an eluent intake aperture 14M.

Figure 13A:
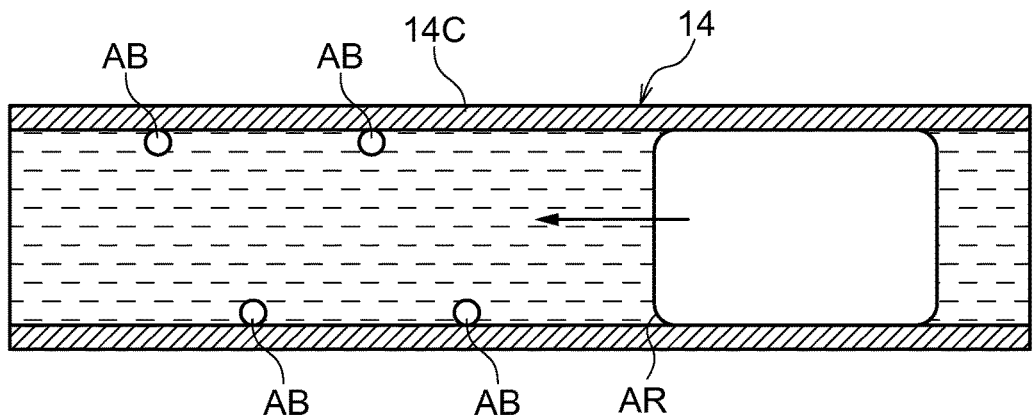
FIG. 13A, FIG. 13B and FIG. 13C are explanatory diagrams showing a sequence in which bubbles in a channel are reduced in accordance with the present invention.
Figure 13B:
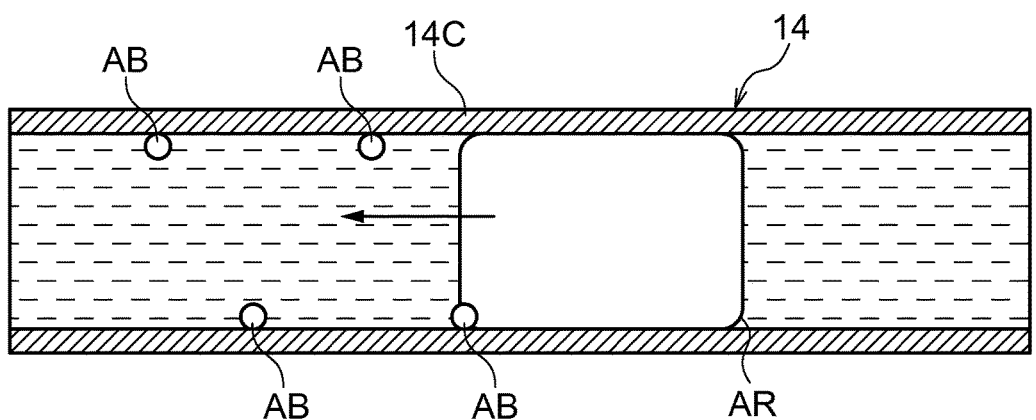
Figure 13C:
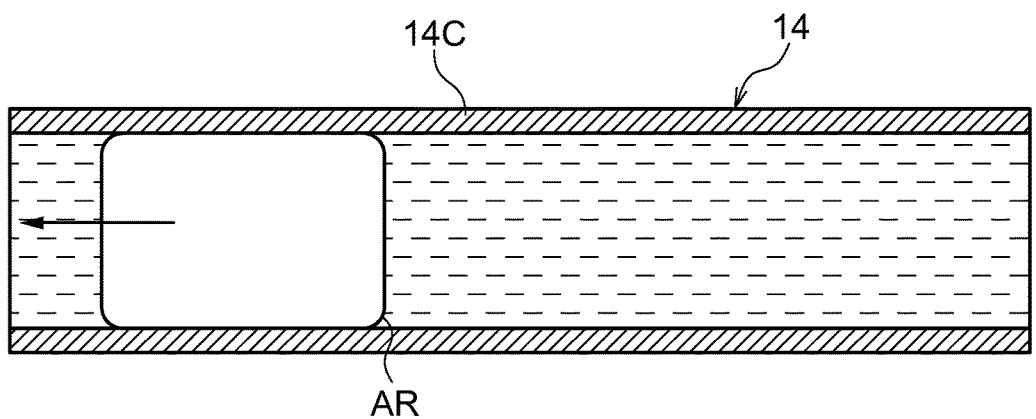

As shown in FIG. 13A, the air layer AR travels inside the first channel 14 (an air layer travel step). Bubbles AB adhere to the inner face of the pipe 14C at the forward side relative to the air layer AR (the left side of the air layer AR in the drawing). As shown in FIG. 13B, when these bubbles AB come into contact with the traveling air layer AR, the bubbles AB are successively taken into the air layer AR. Thus, as shown in FIG. 13C, bubbles inside the first channel 14 are reduced (and preferably eliminated) in portions through which the air layer AR has passed (the right side of the air layer AR in the drawing).

The air layer AR is discharged through the eluent intake aperture 14M into the eluent pack 12A. Thus, a state may be realized in which bubbles AB are decreased in a region of the first channel 14 extending from the syringe 65 to the eluent pack 12A (i.e., substantially the whole of the first channel 14).

The amount by which the plunger 66 is pushed up may be memorized in advance at the control section, as a movement distance or a driving time. A method is also possible in which a sensor or the like detects when the whole of the air layer AR in the syringe 65 has been discharged and the plunger 66 is stopped.

Figure 9:
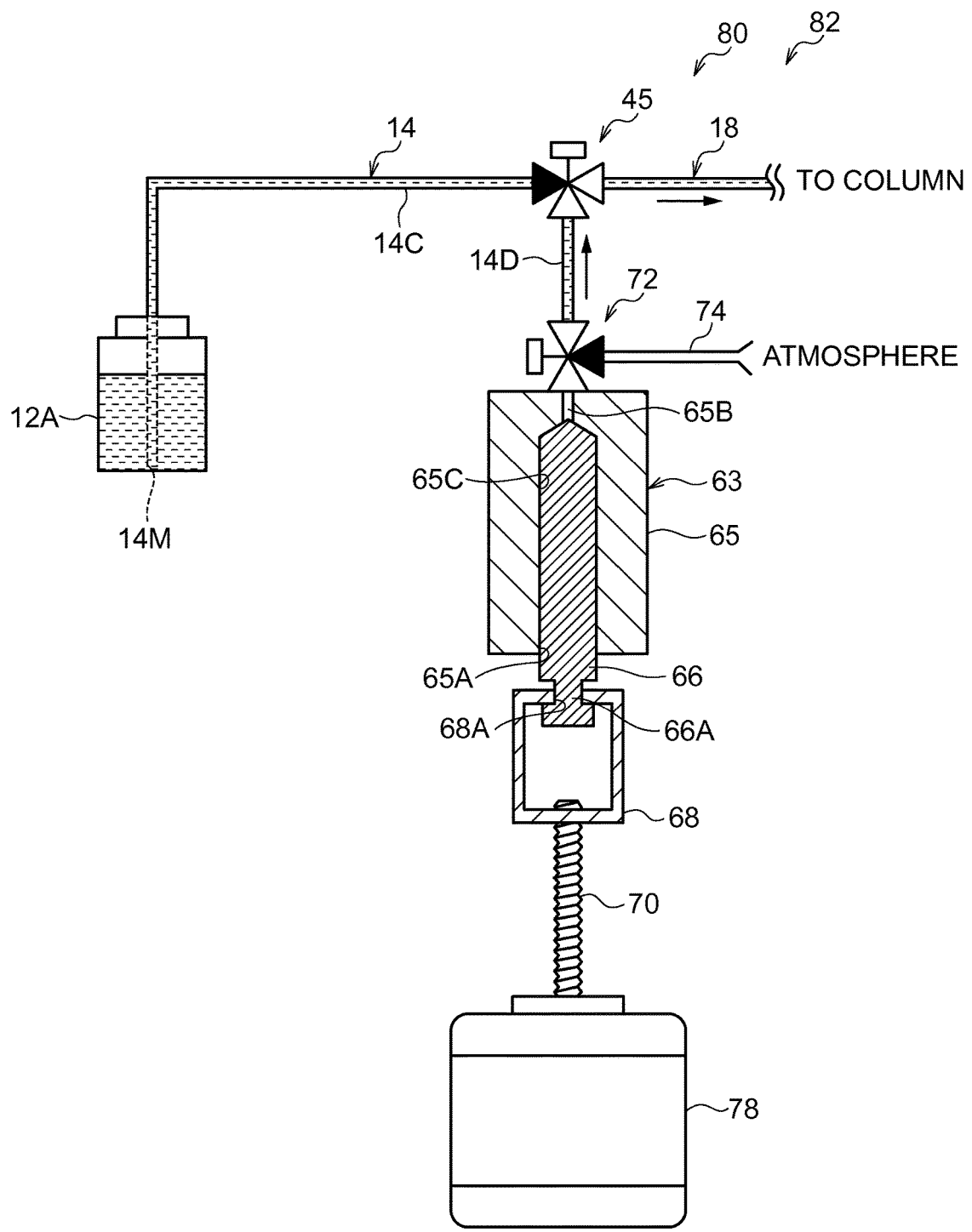
FIG. 9 is an enlarged diagram of principal portions, showing a state in which an eluent is being supplied to a column by the liquid provision device including the channel bubble reduction device in accordance with the first exemplary embodiment of the present invention.

To send eluent in the eluent pack 12A to the column 60, the plunger 66 is temporarily pulled down with the first switching valve 45 staying in the first communication state. Thus, the eluent is introduced into the syringe 65. Then, as shown in FIG. 9, the first switching valve 45 is switched to the second communication state, the plunger 66 is pushed up, and the eluent moves to the column 60 side.

As is clear from the above descriptions, in the present exemplary embodiment there is no need for a degassing device or the like for bubbles in the first channel 14 to be reduced. Therefore, the channel bubble reduction device 80 may be reduced in size and the liquid provision device 82 may be reduced in size. Thus, the chromatography device 1 including the liquid provision device 82 may also be reduced in size.

In a channel bubble reduction method, the atmosphere release valve 72 is opened under a predetermined condition (a timing) and the air layer AR is formed, after which (the atmosphere release valve 72 is closed and) the plunger 66 is pushed up. Bubbles in the first channel 14 may be reduced and the air layer AR may be discharged outside the first channel 14 with just this simple operation.

In the first exemplary embodiment, an example is given in the above descriptions in which the air layer is introduced by the atmosphere release valve 72 (and the atmosphere release pipe 74) provided at the first channel 14. However, an atmosphere release portion may, for example, be formed at the syringe 65. Moreover, the length of the atmosphere release pipe 74 is not particularly limited; a shorter structure than in the illustrated example may be used (such as a structure in which there is substantially no atmosphere release pipe 74 and the atmosphere release valve 72 opens to the atmosphere directly).

Second Exemplary Embodiment

Figure 10:
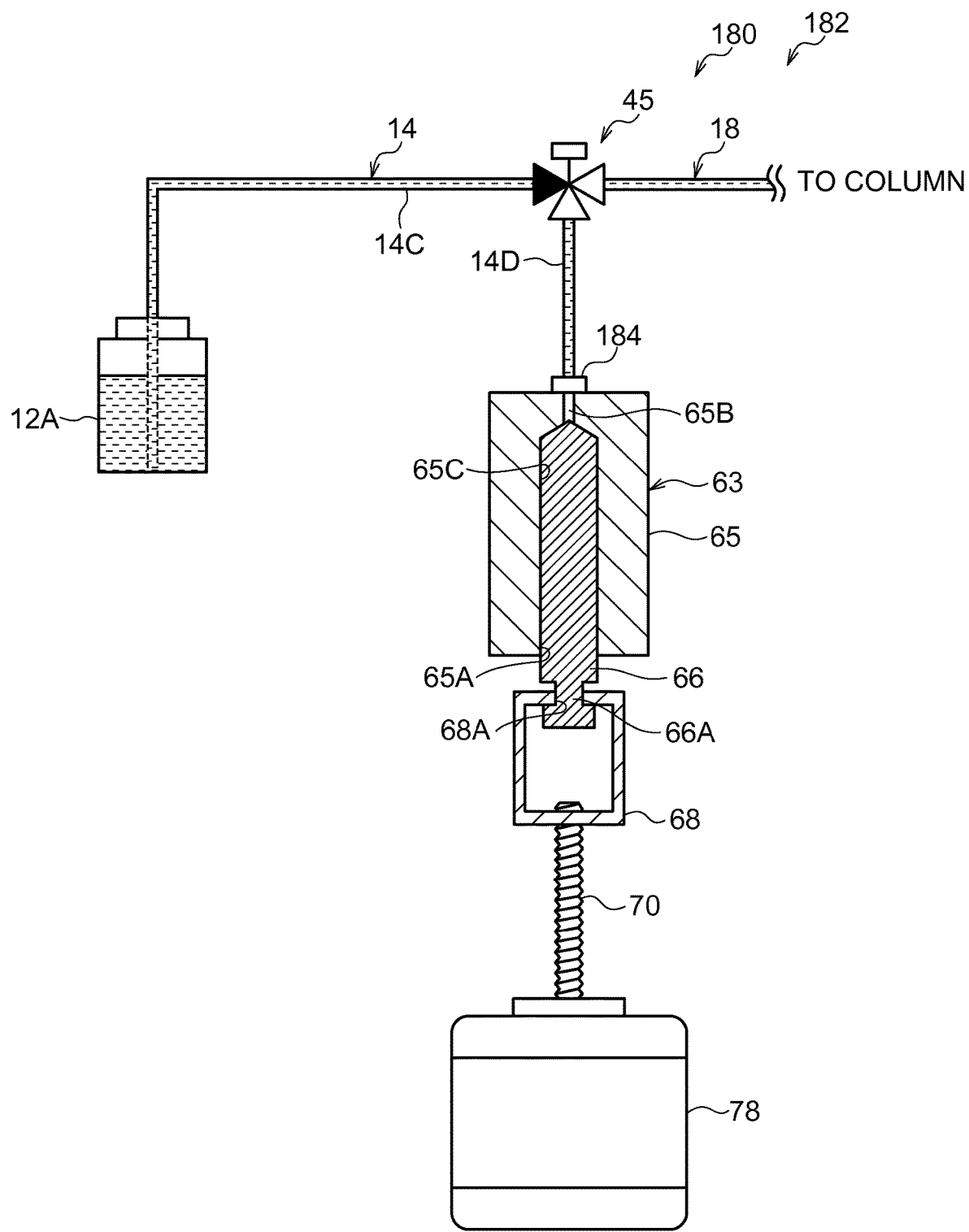
FIG. 10 is an enlarged diagram of principal portions, showing a state before an air layer is formed by a channel bubble reduction device in accordance with a second exemplary embodiment of the present invention.

Next, a channel bubble reduction device 180 according to a second exemplary embodiment of the present invention is described. FIG. 10 shows a liquid provision device 182 equipped with the channel bubble reduction device 180 in accordance with the second exemplary embodiment of the present invention. In this second exemplary embodiment, the overall structure of the chromatography device is the same as in the first exemplary embodiment, so is not described here. Structural elements, members and the like of the second exemplary embodiment that are the same as in the first exemplary embodiment are assigned the same reference numerals and are not described in detail.

In the second exemplary embodiment, the atmosphere release valve 72 and the atmosphere release pipe 74 (see FIG. 4 to FIG. 7) are not provided at the first channel 14. Instead, a heating apparatus 184 is provided. The heating apparatus 184, by locally heating the first channel 14, raises the temperature of the eluent in the first channel 14 and forms an air layer AR. The heating apparatus 184 is controlled by the control section 100 (see FIG. 3).

That is, in the second exemplary embodiment, a structure and method tor forming the air layer AR in the first channel 14 differ from the first exemplary embodiment. However, after the air layer AR has been formed in the first channel 14, the air layer AR is caused to travel to the eluent intake aperture 14M side of the first channel 14 by the plunger 66 being pushed up and reduces bubbles in the first channel 14, the same as in the first exemplary embodiment. Then, the air layer AR is discharged into the eluent pack 12A.

In the second exemplary embodiment, the specific structure of the heating apparatus 184 is not particularly limited provided the heating apparatus 184 can apply heat to an extent capable of forming the air layer AR in the first channel 14 as mentioned above.

Third Exemplary Embodiment

Figure 11:
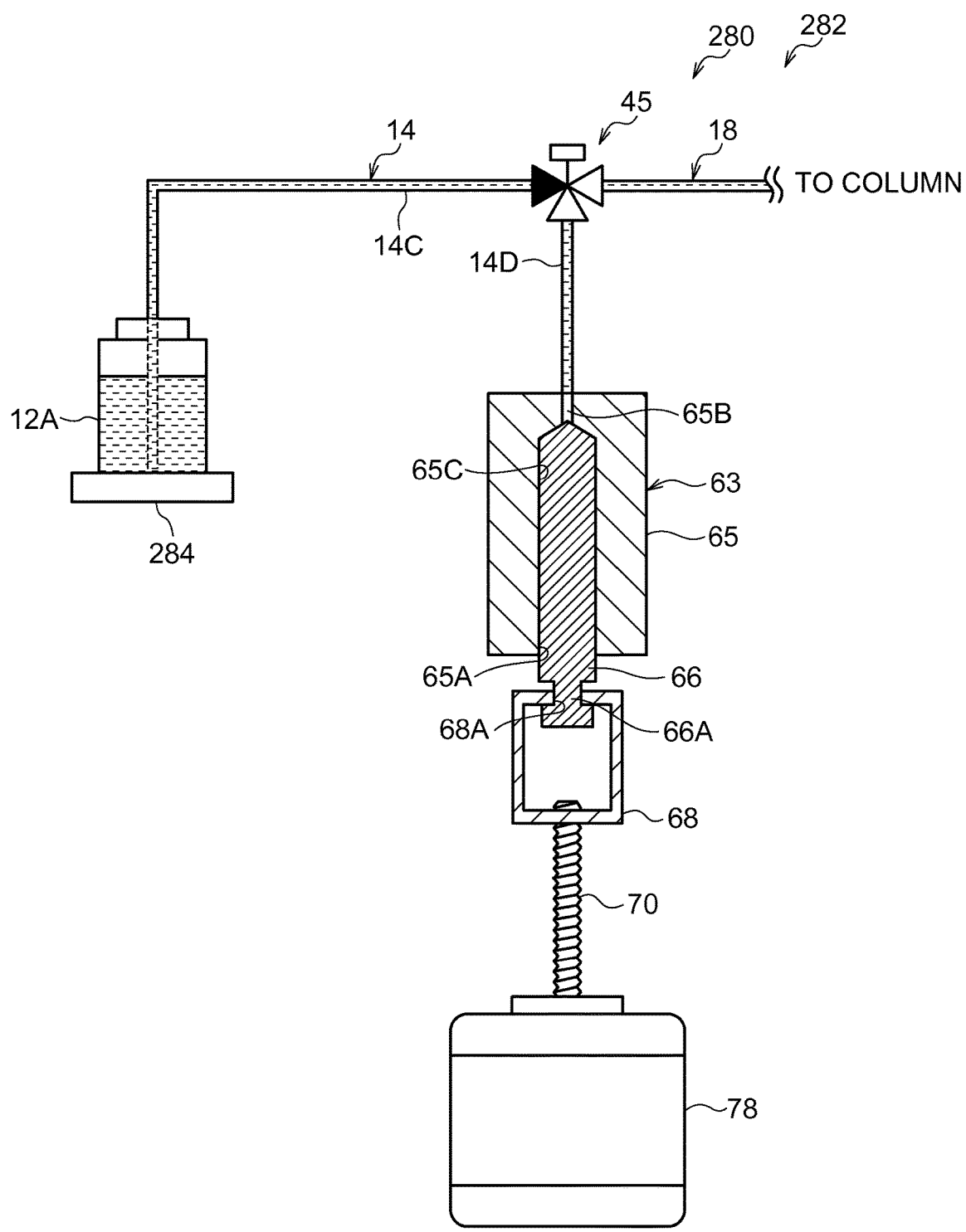
FIG. 11 is an enlarged diagram of principal portions, showing a state before an air layer is formed by a channel bubble reduction device in accordance with a third exemplary embodiment of the present invention.

FIG. 11 shows a liquid provision device 282 equipped with a channel bubble reduction device 280 in accordance with a third exemplary embodiment of the present invention. In this third exemplary embodiment, the overall structure of the chromatography device is the same as in the first exemplary embodiment, so is not described here. Structural elements, members and the like of the third exemplary embodiment that are the same as in the first exemplary embodiment are assigned the same reference numerals and are not described in detail.

In the third exemplary embodiment, neither the atmosphere release valve 72 and atmosphere release pipe 74 (see FIG. 4 to FIG. 7) nor the heating apparatus 184 (see FIG. 10) are provided at the first channel 14. Instead, an elevation stand 284 supports the eluent pack 12A to be capable of raising and lowering the eluent pack 12A. The elevation stand 284 is controlled by the control section 100 (see FIG. 3).

Figure 12A:
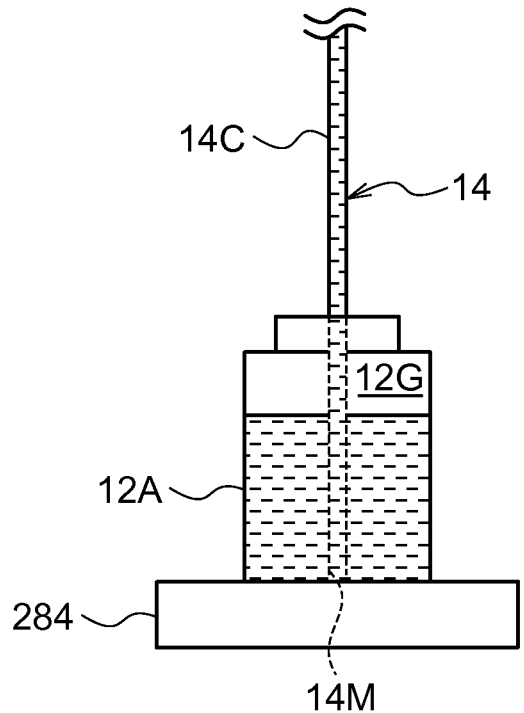
FIG. 12A is an enlarged diagram of principal portions in which a vicinity of an eluent pack of the channel bubble reduction device in accordance with the third exemplary embodiment of the present invention is shown enlarged, in the state before the air layer is formed.

As can be seen in FIG. 12A, there is a gas layer 12G at an upper portion of the interior of the eluent pack 12A, and the eluent is at a lower portion of the interior of the eluent pack 12A. In a usual state, the elevation stand 284 supports the eluent pack 12A at a position at which the eluent intake aperture 14M of the first channel 14 is submerged in the eluent (a submerged position). The eluent pack 12A may lower the eluent pack 12A to a position at which the eluent intake aperture 14M is separated from the eluent in the eluent pack 12A and is in the gas layer 12G (a separated position).

In the third exemplary embodiment of the structure described above, the air layer AR is formed in the first channel 14 by the following procedure. Usually, as shown in FIG. 12A, the first switching valve 45 is in the first communication state and the eluent intake aperture 14M is at the submerged position.

Figure 12B:
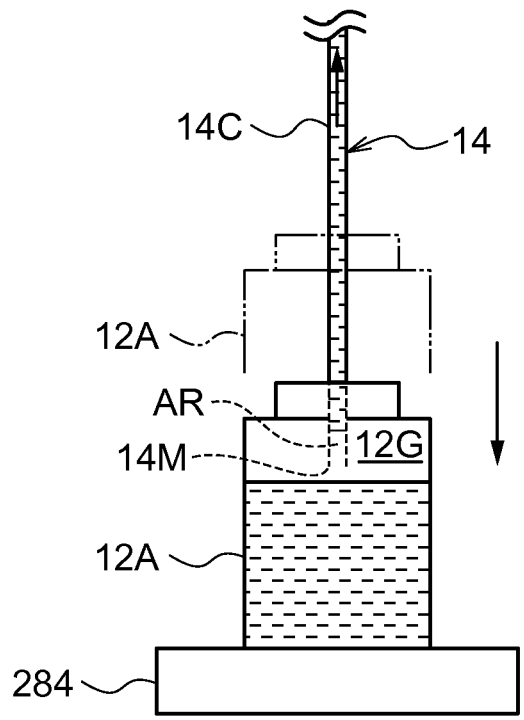
FIG. 12B is an enlarged diagram of principal portions in which the vicinity of the eluent pack of the channel bubble reduction device in accordance with the third exemplary embodiment of the present invention is shown enlarged, in a state in which the air layer is traveling in a channel.

Then, as shown in FIG. 12B, the elevation stand 284 is lowered, and the eluent pack 12A is lowered. Thus, the eluent intake aperture 14M is relatively raised, to the separated position.

The plunger 66 is pulled down and air in the gas layer 12G is taken into the first channel 14 through the eluent intake aperture 14M, forming the air layer AR. In this state, the plunger 66 is pulled down further, and the air layer AR travels in the first channel 14 to the plunger pump 63 side thereof. The air layer AR is caused to travel to a predetermined position (preferably inside the syringe 65). Then the plunger 66 is pushed up, and the air layer AR is caused to travel toward the eluent intake aperture 14M (in essence, the air layer AR travels forward and backward in the first channel 14). The same as in the first exemplary embodiment and the second exemplary embodiment, the air layer AR is discharged through the eluent intake aperture 14M into the eluent pack 12A. At this time it is acceptable for the eluent intake aperture 14M to be at the submerged position and the air layer AR to be discharged into the eluent.

Thus, in the third exemplary embodiment too, bubbles are taken into the air layer AR in regions of the interior of the first channel 14 through which the air layer AR travels, and bubbles in the first channel 14 may be reduced.

Furthermore, in the third exemplary embodiment there is no need to provide the atmosphere release valve 72 and atmosphere release pipe 74 of the first exemplary embodiment or the heating apparatus 184 of the second exemplary embodiment, or the like. Therefore, a further reduction in size may be possible.

In the third exemplary embodiment, an example is described above in which the elevation stand 284 supporting the eluent pack 12A is raised and lowered and thus the eluent pack 12A supported by the elevation stand 284 is raised and lowered. However, it is sufficient for the eluent pack 12A and the eluent intake aperture 14M of the first channel 14 to move relatively, to move the eluent intake aperture 14M between the submerged position and the separated position. For example, a structure is possible in which the eluent pack 12A cannot be raised and lowered but at least a portion of the first channel 14 in the vicinity of the eluent intake aperture 14M can be raised and lowered.

In the exemplary embodiments described above, examples are described in which the air layer AR in the first channel 14 is discharged outside the first channel 14 through the eluent intake aperture 14M. However, a structure is possible in which, for example, an air layer discharge aperture is provided at the first channel 14 and the air layer AR is discharged through this air layer discharge aperture (which may be shut off at usual times by a shut-off valve or the like). However, in a structure in which the air layer AR is discharged through the eluent intake aperture 14M, the air layer AR may be caused to travel and reduce bubbles over a longer range.

As illustrated in FIG. 4 and the like, in the eluent pack 12A, bubbles AB tend to adhere to the vicinity of the eluent intake aperture 14M. When the air layer AR is discharged from the eluent intake aperture 14M, the bubbles AB may be taken into the air layer AR. Thus, the effect of reducing bubbles is enhanced.

It is also possible to employ a structure in which the air layer AR is not discharged from the first channel 14. It is at least not necessary to discharge the air layer AR from the first channel 14 each time the operation of reducing bubbles is carried out (the operation of causing the air layer AR to travel in the first channel 14). For example, if the first switching valve 45 is switched from the first communication state to the second communication state in a state in which the plunger 66 has been pushed up and the air layer AR caused to travel to a predetermined position of the first channel 14 (a position at the eluent intake aperture 14M side relative to the first switching valve 45), the eluent remaining in the syringe 65 may be sent through the second channel 18 to the column 60. In this structure, if the volume of the syringe 65 is sufficiently large and the plunger 66 has been pulled down and a larger amount of the eluent introduced into the syringe 65 in the state in which the air layer AR is present in the syringe 65, an amount of liquid that is supplied to the column 60 by one operation of pushing of the plunger 66 may be assuredly large. However, if this operation is repeatedly carried out without the air layer AR being discharged outside the first channel 14, the air layer AR in the first channel 14 will progressively get larger. Therefore, it is preferable to include the operation of discharging the enlarged air layer AR outside the first channel 14 as appropriate.

As shown in FIG. 2, the chromatography device according to the exemplary embodiments described above has a structure that only degasses the eluent A accommodated in the eluent pack 12A, but this is not limiting. As appropriate, the switching valves 41 and 43 may be switched and the eluent packs 12B and 12C may be similarly degassed by the plunger pump 63. Further, respective pumps the same as the plunger pump 63 may be connected to the eluent packs 12B and 12C and bubbles may be reduced in all of the eluents.

In the above descriptions, an example is described in which bubbles are reduced in the flow of supply of an eluent, but the liquid flowing in the channel is not limited to an eluent. That is, the present invention may be applied when bubbles in a channel connecting an aperture of a liquid supply apparatus with a liquid accommodation portion (the first channel) are to be reduced, regardless of the type of liquid flowing in the channel. Further, the liquid provision device is not limited to a liquid provision device provided in a chromatography device. That is, the destination of the supply of liquid by the liquid provision device is not particularly limited; the effects of bubbles when a liquid is used at a supply destination may be moderated.

When the present invention is configured as described above, bubbles in a channel may be decreased.

All cited documents, patent applications and technical standards mentioned in the present specification are incorporated by reference in the present specification to the same extent as if the individual cited documents, patent applications and technical standards were specifically and individually incorporated by reference in the present specification.

What is claimed is:

1. A channel bubble reduction device, comprising:
    a liquid accommodation portion that accommodates a liquid;
    a liquid supply apparatus that, with a pushing operation of a rod, discharges the liquid through an aperture portion of a tube portion;
    a first channel that connects the aperture portion of the liquid supply apparatus with the liquid accommodation portion;
    an air layer formation apparatus that forms an air layer in the first channel; and
    a controller that controls the channel bubble reduction device, wherein
    the air layer formation apparatus includes:
        an atmosphere release aperture provided at the first channel or the tube portion; and
        an opening and closing valve capable of opening and closing the atmosphere release aperture, and
    the controller controls the channel bubble reduction device so as to introduce air through the atmosphere release aperture into the first channel with a pulling operation of the rod and to discharge the air layer externally from the first channel with the pushing operation of the rod.

2. The channel bubble reduction device according to claim 1, wherein the liquid supply apparatus discharges the air layer externally from the first channel with the pushing operation of the rod.

3. The chromatography device, comprising:
    a liquid provision device, comprising:
        the channel bubble reduction device according to claim 2;
        a second channel branching from the first channel; and
        a first switching valve provided at a branching portion of the second channel and configured to switch so as to put the liquid supply apparatus side of the first channel into fluid communication with either the liquid accommodation portion or the second channel;
    an adsorption portion that adsorbs an analysis component in the liquid supplied by the liquid provision device; and
    an analysis device that analyzes the analysis component, which is eluted by the liquid supplied to the adsorption portion by the liquid provision device.

4. The channel bubble reduction device according to claim 1, wherein:
    the air layer formation apparatus includes a movement apparatus that relatively moves a liquid intake aperture at the liquid accommodation portion side of the first channel between a submerged position at which the liquid intake aperture is submerged in the liquid and a separated position at which the liquid intake aperture is separated from the liquid; and
    the liquid supply apparatus introduces air through the liquid intake aperture at the separated position into the first channel with a pulling operation of the rod.

5. The chromatography device, comprising:
    a liquid provision device, comprising:
        the channel bubble reduction device according to claim 4;
        a second channel branching from the first channel; and
        a first switching valve provided at a branching portion of the second channel and configured to switch so as to put the liquid supply apparatus side of the first channel into fluid communication with either the liquid accommodation portion or the second channel;
    an adsorption portion that adsorbs an analysis component in the liquid supplied by the liquid provision device; and
    an analysis device that analyzes the analysis component, which is eluted by the liquid supplied to the adsorption portion by the liquid provision device.

6. A chromatography device, comprising:
    a liquid provision device, comprising:
        the channel bubble reduction device according to claim 1;
        a second channel branching from the first channel; and
        a first switching valve provided at a branching portion of the second channel and configured to switch so as to put the liquid supply apparatus side of the first channel into fluid communication with either the liquid accommodation portion or the second channel;
    an adsorption portion that adsorbs an analysis component in the liquid supplied by the liquid provision device; and
    an analysis device that analyzes the analysis component, which is eluted by the liquid supplied to the adsorption portion by the liquid provision device.

* * * * *